(12) United States Patent
Young et al.

(10) Patent No.: US 8,241,870 B2
(45) Date of Patent: Aug. 14, 2012

(54) MAMMALIAN EXPRESSION VECTOR WITH A HIGHLY EFFICIENT SECRETORY SIGNAL SEQUENCE

(75) Inventors: Robert Young, London (GB); James Rance, London (GB)

(73) Assignee: Lonza Biologics PLC, Slough (GB)

( * ) Notice: Subject to any disclaimer, the term of this patent is extended or adjusted under 35 U.S.C. 154(b) by 314 days.

(21) Appl. No.: 12/601,037

(22) PCT Filed: Jun. 3, 2008

(86) PCT No.: PCT/EP2008/004413
§ 371 (c)(1),
(2), (4) Date: Apr. 2, 2010

(87) PCT Pub. No.: WO2008/148519
PCT Pub. Date: Dec. 11, 2008

(65) Prior Publication Data
US 2010/0240097 A1    Sep. 23, 2010

(30) Foreign Application Priority Data

Jun. 4, 2007   (GB) .................................. 0710614.9

(51) Int. Cl.
*C12P 21/06*     (2006.01)
*C12N 15/00*    (2006.01)
*C07H 21/02*    (2006.01)
*C07K 14/00*    (2006.01)

(52) U.S. Cl. ................... 435/69.1; 435/320.1; 536/23.1; 530/300

(58) Field of Classification Search .................. 530/300; 536/23.1; 435/320.1, 69.1
See application file for complete search history.

(56) References Cited

U.S. PATENT DOCUMENTS

| 5,633,162 A | 5/1997 | Keen et al. |
| 2006/0121604 A1 | 6/2006 | Handa et al. |

FOREIGN PATENT DOCUMENTS

| JP | 2004187652 | 7/2004 |
| WO | 94/02592 A1 | 2/1994 |
| WO | 2006/132350 A1 | 12/2006 |
| WO | 2007/144990 A1 | 12/2007 |

OTHER PUBLICATIONS

Nakajima et al., "cDNA cloning and characterization of a secreted luciferase from the luminous Japanese ostracod, *Cypridina noctiluca*", Bioscience Biotechnology Biochemistry, Japan Soc. for Bioscience, Biotechnology and Agrochemistry, vol. 28, No. 3, pp. 565-570; 2004.

Yamagishi et al., "Perfusion-Culture-Based Secreted Bioluminescence Reporter Assay in Living Cells", Analytical Biochemistry, vol. 354, No. 1, pp. 15-21; 2006.

Brown et al., "Process Development for the Production of Recombinant Antibodies Using the Glutamine Synthetase (GS) System", Cytotechnology, vol. 9, pp. 231-236; 1992.

Simonsen et al., "Isolation and Expression of an Altered Mouse Dihydrofolate Reductase cDNA", Biochemistry, vol. 80, pp. 2495-2499; 1983.

Bebbington et al., "High-Level Expression of a Recombinant Antibody from Myeloma Cells Using a Glutamine Synthetase Gene as an Amplifiable Selectable Marker", Bio/Technology, vol. 10, pp. 169-175; 1992.

Cockett et al., "High Level Expression of Tissue Inhibitor of Metalloproteinases in Chinese Hamster Ovary Cells Using Glutamine Synthetase Gene Amplification", Bio/Technology, vol. 8, pp. 662-667; 1990.

Iscove et al., "Complete Replacement of Serum by Albumin, Transferrin, and Soybean Lipid in Cultures of Lipopolysaccharide-Reactive B Lymphocytes", Journal of Experimental Medicine, vol. 47, pp. 923-933; 1978.

Puck et al., "Genetics of Somatic Mammalian Cells* III. Long-Term Cultivation of Euploid Cells from Human and Animal Subjects", Journal of Experimental Medicine, vol. 108, pp. 945-955; 1958.

Urlaub et al., "Isolation of Chinese Hamster Cell Mutants Deficient in Dihydrofolate Reductase Activity", Proceedings of the National Academy of Sciences, vol. 77, pp. 4216-4222-; 1980.

Albert Leibovitz, "The Growth and Maintenance of Tissue-Cell Cultures in Free Gas Exchange with the Atmosphere", American Journal of Hygiene, vol. 78, pp. 173-180; 1963.

Moore et al., "Cultural of Normal Human Leukocytes", Journal of the American Medical Association, vol. 199, No. 8, pp. 519-524; 1967.

Richard G. Ham, "Clonal Growth of Mammalian Cells in a Chemically Defined, Synthetic Medium, Proceedings of the National Academy of Sciences", vol. 53, pp. 288-293; 1965.

Tanaka et al., "Homologues of fibroin L-chain and P25 of *Bombyx mori* are present in *Dendrolimus spectabilis* and *Papilio xuthus* but not detectable in *Antheraea yamanai*", Insect Biochemistry and Molecular Biology, vol. 31, pp. 665-677; 2001.

Database UniProt [On-line], "SubName: Full=Fibroin L-chain;" XP002520171 retrieved from EBI accession No. UNIPROT:Q9BLL7.

*Primary Examiner* — Karen Cochrane Carlson
(74) *Attorney, Agent, or Firm* — Hoffmann & Baron, LLP

(57) ABSTRACT

The present invention relates to a mammalian cell based expression and secretion system and the expression and secretion of recombinant proteins by using secretory signal peptides. The present invention also relates to an expression cassette useful for the secretion of a heterologous gene from a mammalian cell, in particular a CHO cell. The present invention is also directed to a method of secreting a heterologous protein from mammalian cells such as CHO cells.

6 Claims, 4 Drawing Sheets

MAMMALIAN EXPRESSION VECTOR WITH A HIGHLY EFFICIENT SECRETORY SIGNAL SEQUENCE

Figure 1:
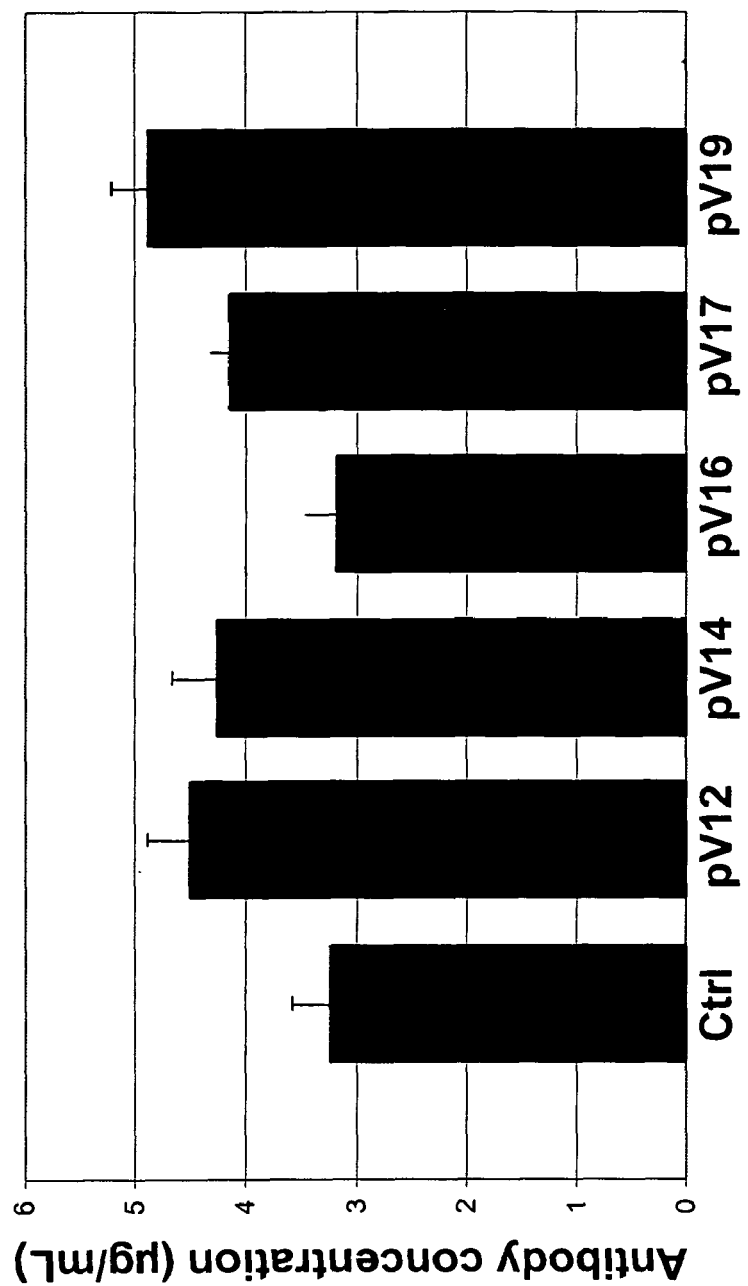

This application is the U.S. National Phase of, and Applicants claim priority from, International Application Number PCT/EP2008/004413 filed 3 Jun. 2008 and United Kingdom Patent Application bearing Serial No. GB0710614.9 filed 4 Jun. 2007, each of which are incorporated herein by reference in their entirety.

INCORPORATION OF SEQUENCE LISTING

Incorporated herein by reference in its entirety is the Sequence Listing for the above-identified Application. The Sequence Listing is disclosed on a computer-readable ASCII text file titled "Sequence_Listing_1686-199PCTUS.txt", created on May 25, 2010. The sequence.txt file is 2.30 KB.

BACKGROUND OF THE INVENTION

The present invention relates to mammalian cell based expression systems and the expression and secretion of recombinant proteins by using secretory signal peptides. The present invention also relates to an expression cassette useful for the secretion of a heterologous gene from a mammalian cell, in particular a CHO cell. The present invention is also directed to methods of secreting a heterologous protein from mammalian cells such as CHO cells and methods for the production of secreted recombinant proteins in mammalian host cells.

Recombinant polypeptides for medical, research and veterinary applications such as antibodies are produced using a wide variety of genetically engineered organisms that include prokaryotic and eukaryotic cells. However, a lot of these proteins are glycoproteins requiring post-translational modifications. Thus, prokaryotic host cells such as bacterial cells are not suitable. For this reason other protein expression systems were developed using the cells of higher eukaryotes, e.g. insect cells or mammalian cells. Viral expression systems can produce recombinant proteins both in insects and mouse cell lines but suffer from several serious drawbacks, in particular that purification of recombinant proteins from virus infected systems is very problematic.

A major problem in biotechnology exists in the production and recovery of recombinant polypeptides that are not readily secreted such as intracellular proteins or protein subunits, from genetically engineered organisms. Often these intracellular proteins or protein subunits can be expressed at only moderate levels inside a cell and their purification must first include steps to lyse the cells, followed by several procedures to isolate the desired polypeptides from the other intracellular proteins.

One approach to solve these problems is to have recombinant proteins secreted into the periplasmic space or culture medium. Whenever possible, secretion is the preferred strategy since it permits easy and efficient purification from the extracellular medium. In addition, the secretory production of recombinant proteins has the advantage that proteolytic degradation may be avoided and that there is a better chance of correct protein folding. Successful protein secretion requires effective translocation of the protein across the endoplasmatic reticulum or plasma membrane. Proteins that are secreted from a cell through a cell membrane are generally produced within the cell in a precursor form, referred to as a "preprotein". This "preprotein" form includes an additional peptide sequence at the amino-terminus which is required to target the nascent peptide chain to the endoplasmatic reticulum to enable its entry into the secretory pathway. This additional peptide sequence is referred to as a signal sequence.

However, it is known that secretion frequently does not function to the degree desired, for example because the native signal sequence of the recombinant protein often does not operate well in the host cell. To date, each expression system needs specific tailoring to meet the requirements for each protein product to ensure correct folding, activity and desired yield. Although quite a lot of signal sequences have been identified which might be useful for the secretion of particular recombinant proteins, there is still a need in the art for additional signal sequences that can promote efficient secretion of recombinant proteins, in particular immunoglobulins, in mammalian host cells.

Thus, the technical problem underlying the present invention is to provide a method to efficiently secrete non-secretion competent polypeptides, in particular antibody chains from a eukaryotic host cell such as a Chinese Hamster Ovary (CHO) cell.

The present invention solves this technical problem by providing an expression cassette for the secretion of a heterologous protein from a mammalian host cell, in particular a CHO cell comprising a promoter, functionally linked to a DNA sequence encoding a signal peptide which is linked in frame to a DNA sequence encoding a heterologous protein, wherein the DNA sequence encoding the signal peptide is selected from the group consisting from SEQ ID No. 2, SEQ No. 4, SEQ ID No. 6, SEQ ID No. 8, SEQ ID No.10 or a DNA sequence encoding an amino acid sequence depicted in SEQ ID No. 1, SEQ ID No. 3, SEQ ID No. 5, SEQ ID No. 7 or SEQ ID No. 9.

DESCRIPTION OF THE INVENTION

It was found by the inventors of the present invention that the signal sequences employed in the expression cassettes provide for a proper processing and an efficient secretion of operably linked polypeptide sequences in mammalian host cells. As an initial screen, nineteen different signal sequences have been tested that were derived from different secreted proteins of different species to the CHO cells routinely used for recombinant protein production whereby only 5 of them resulted in an improved secretion of the polypeptides tested. Thus, the experiments, demonstrated that it is generally unpredictable whether a signal sequence from one species would be functional in another species.

Two of the five signal sequences, namely V19 (SEQ ID No. 9) and V17 (SEQ ID No. 7), resulted in cell lines with a particularly strong increase in mean antibody concentration over control cell lines.

On the basis of the amino acid sequence of signal peptide V19 the following consensus amino acid sequence of a signal peptide was derived: MMRP[hydrophobic amino acid]$_n$ TSALA. On the basis of the amino acid sequence of signal peptide V17 the following consensus amino acid sequence of a signal peptide was derived: MKT[hydrophobic amino acid]$_n$ CATVHC.

Thus, the present invention solves the technical problem also by providing a signal sequence with the general amino acid sequence MMRP[hydrophobic amino acid]$_n$ TSALA and also a signal sequence with the general amino acid sequence MKT[hydrophobic amino acid]$_n$ CATVHC. Both signal sequences provide for an efficient secretion of operably linked polypeptide sequences, e.g. antibody chains, in mammalian host cells such as CHO cells. Preferably the hydrophobic amino acid in the central region is selected from the group consisting of alanine (Ala or A), isoleucine (Ile or I), leucine (Leu or L), phenylalanine (Phe or F), methionine (Met or M) and valine (Val or V). Ala has a hydropathy index of 1.8. Ile has a hydropathy index of 4.5. Leu has a hydropathy index of 3.8. Phe has a hydropathy index of 2.8. Met has a hydropathy index of 1.9. Val has a hydropathy index of 4.2. Preferably the central stretch of hydrophobic amino acids consists especially of Leu (L) with some occurrence of Val, Ala, Phe and Ile. Preferably the central hydrophobic stretch has a length of 4 to 9 amino acid residues. Preferably the central hydrophobic region comprises 4-16 amino acid residues, particularly preferred 4-9 residues.

The present invention also relates to an expression cassette for the secretion of a heterologous protein from a mammalian host cell comprising a promoter, functionally linked to a DNA sequence encoding a signal peptide which is linked in frame to a DNA sequence encoding a heterologous protein, wherein the DNA sequence encoding the signal peptide is selected from a DNA sequence encoding the amino acid sequence [hydrophobic amino acid]$_n$ TSALA or a DNA sequence encoding the amino acid sequence MKT[hydrophobic amino acid]$_n$ CATVHC whereby n is an integer of 4 to 16 and the hydrophobic amino acid is selected from the group consisting of alanine, isoleucine, leucine, phenylalanine, methionine and valine.

In a particularly preferred embodiment the DNA sequence encoding the signal sequence is selected from SEQ ID No. 8 or SEQ ID No.10 or a DNA sequence encoding the amino acid sequence depicted in SEQ ID No. 7 or SEQ ID No. 9.

The present invention also relates to an expression cassette for the secretion of a heterologous protein from a mammalian host cell comprising a promoter, functionally linked to a DNA sequence encoding a signal peptide which is linked in frame to a DNA sequence encoding a heterologous protein, wherein the DNA sequence encoding the signal peptide is selected from the group consisting from SEQ ID No. 2, SEQ No. 4, SEQ ID No. 6, SEQ ID No. 8, SEQ ID No.10 or a DNA sequence encoding an amino acid sequence depicted in SEQ ID No. 1, SEQ ID No. 3, SEQ ID No. 5, SEQ ID No. 7 or SEQ ID No. 9

In the context of the present invention an "expression cassette" is made up of one or more genes to be expressed and sequences controlling their expression such as a promoter/enhancer sequence, including any combination of cis-acting transcriptional control elements. The sequences controlling the expression of the gene, i.e. its transcription and the translation of the transcription product, are commonly referred to as regulatory unit. Most parts of the regulatory unit are located upstream of coding sequence of the heterologous gene and are operably linked thereto. The expression cassette may also contain a downstream 3' untranslated region comprising a polyadenylation site. The regulatory unit of the invention is either directly linked to the gene to be expressed, i.e. transcription unit, or is separated therefrom by intervening DNA such as for example by the 5'-untranslated region of the heterologous gene. Preferably the expression cassette is flanked by one or more suitable restriction sites in order to enable the insertion of the expression cassette into a vector and/or its excision from a vector. Thus, the expression cassette according to the present invention can be used for the construction of an expression vector, in particular a mammalian expression vector.

In the context of the invention the terms "heterologous coding sequence", "heterologous gene sequence", "heterologous gene", "recombinant gene" or "gene of interest" are used interchangeably. These terms refer to a DNA sequence that codes for a recombinant or heterologous protein product that is sought to be expressed in the mammalian cell and harvested in high amount. The product of the gene can be a protein or polypeptide, but also a peptide. The heterologous gene sequence is naturally not present in the host cell and is derived from an organism of a different species.

The product of the gene may be any protein of interest, e.g. a therapeutic protein such as an interleukin or an enzyme or a subunit of a multimeric protein such as an antibody or a fragment thereof. Preferably, the protein is an antibody or engineered antibody or a fragment thereof, most preferably it is an Immunoglobulin G (IgG) antibody.

According to the present invention the terms "signal peptide" or "signal sequence" are used interchangeably and refer to a short continuous stretch of amino acids residues at the amino-terminus of secreted and membrane-bound proteins. The signal peptide targets the protein to the secretory pathway and is cleaved from the nascent chain once translocated in the reticulum endoplasmatic membrane. The signal peptide consists of three regions: an amino-terminal polar region (N region), where frequently positive charged amino acid residues are observed, a central hydrophobic region (H region) of 7-8 amino acid residues and a carboxy-terminal region (C region) that includes the cleavage site. The cleavage of the signal peptide from the mature protein occurs at this cleavage site.

A "promoter" is defined as a regulatory DNA sequence generally located upstream of a gene that mediates the initiation of transcription by directing RNA polymerase to bind to DNA and initiating RNA synthesis.

The terms "functionally linked" and "operably linked" are used interchangeably and refer to a functional relationship between two or more DNA segments, in particular gene sequences to be expressed and those sequences controlling their expression. For example, a promoter/enhancer sequence, including any combination of cis-acting transcriptional control elements is operably linked to a coding sequence if it stimulates or modulates the transcription of the coding sequence in an appropriate host cell or other expression system. Promoter regulatory sequences that are operably linked to the transcribed gene sequence are physically contiguous to the transcribed sequence.

Another aspect of the present invention relates to a mammalian expression vector comprising a promoter functionally linked to a DNA sequence encoding a signal peptide which is linked in frame to a DNA sequence encoding a heterologous protein, wherein the DNA sequence encoding the signal peptide is selected from a DNA sequence encoding the amino acid sequence MMRP [hydrophobic amino acid]$_n$ TSALA or a DNA sequence encoding the amino acid sequence MKT [hydrophobic amino acid]$_n$ CATVHC whereby n is an integer of 4 to 16 and the hydrophobic amino acid is A, I, L, M, F or V. Preferably the DNA sequence encoding the signal sequence is selected from SEQ ID No. 8 or SEQ ID No.10 or a DNA sequence encoding an amino acid sequence depicted in SEQ ID No. 7 or SEQ ID No. 9.

The present invention also relates to a mammalian expression vector comprising a promoter, functionally linked to a DNA sequence encoding a signal peptide which is linked in frame to a DNA sequence encoding a heterologous protein, wherein the DNA sequence encoding the signal peptide is selected from the group consisting from SEQ ID No. 2, SEQ No. 4, SEQ ID No. 6, SEQ ID No. 8, SEQ ID No.10 or a DNA sequence encoding an amino acid sequence depicted in SEQ ID No. 1, SEQ ID No. 3, SEQ ID No. 5, SEQ ID No. 7 or SEQ ID No. 9.

Thus, the present invention also relates to mammalian expression vectors comprising an expression cassette for the secretion of a heterologous protein according to the invention.

In the context of the present invention a "mammalian expression vector" is a, preferably isolated and purified, DNA molecule which upon transfection into an appropriate mammalian host cell provides for a high-level expression of a recombinant gene product within the host cell. In addition to the DNA sequence coding for the recombinant or heterologous gene product the expression vector comprises regulatory DNA sequences that are required for an efficient transcription of the DNA coding sequence into mRNA and for an efficient translation of the mRNAs into proteins in the host cell line.

In a preferred embodiment of the invention the mammalian expression vector comprises at least two separate transcription units. An expression vector with two separate transcription units is also referred to as a double-gene vector. An example thereof is a vector, in which the first transcription unit encodes the heavy chain of an antibody or a fragment thereof and the second transcription unit encodes the light chain of an antibody. Another example is a double-gene vector, in which the two transcription units encode two different subunits of a protein such as an enzyme. However, it is also possible that the inventive expression vector comprises more than two separate transcription units, for example three, four or even more separate transcription units each of which comprises a different nucleotide sequence encoding a different polypeptide chain. An example therefore is a vector with four separate transcription units, each of which contains a different nucleotide sequence encoding one subunit of an enzyme consisting of four different subunits.

Preferably, the mammalian expression vectors of the present invention further contain at least one expressible marker selectable in animal cells. Any selection marker commonly employed such as thymidine kinase (tk), dihydrofolate reductase (DHFR) or glutamine synthetase (GS) may be used.

In a particular preferred embodiment, the mammalian expression vector contains a GS selection marker (Bebbington et al., 1992, High-level expression of a recombinant antibody from myeloma cells using a glutamine synthetase gene as an amplifiable selectable marker, Bio/Technology 10:169-175; Cockett et al., 1990, High level expression of tissue inhibitor of metalloproteinases in Chinese Hamster Ovary (CHO) cells using Glutamine synthetase gene amplification, Bio/Technology 8: 662-667). The GS-system is one of only two systems that are of particular importance for the production of therapeutic proteins. In comparison to the dihydrofolate reductase (DHFR) system, the GS system offers a large time advantage during development because highly productive cell lines can often be created from the initial transfectant thus avoiding the need for multiple rounds of selection in the presence of increasing concentrations of selective agent in order to achieve gene amplification (Brown et al., 1992, Process development for the production of recombinant antibodies using the glutamine synthetase (GS) system, Cytotechnology 9:231-236).

Preferably, the expression vectors of the invention also contain a limited number of useful restriction sites for insertion of the expression cassette for the secretion of a heterologous protein of the present invention. Where used in particular for transient/episomal expression only, the expression vectors of the invention may further comprise an origin of replication such as origin of Epstein Barr Virus (EBV) or SV40 virus for autonomous replication/episomal maintenance in eukaryotic host cells but may be devoid of a selectable marker. Transient expression in cell lacking relevant factors to facilitate replication of the vector is also possible.

A further aspect of the present invention relates to a mammalian host cell containing the mammalian expression vector according to the invention. The terms "host cell" or "host cell line" refer to any cells, in particular mammalian cells, which are capable of growing in culture and expressing a desired protein recombinant product protein.

The mammalian host cell can be a human or non-human cell. Preferred examples of the mammalian host cells include, without being restricted to, MRC5 human fibroblasts, 983M human melanoma cells, MDCK canine kidney cells, RF cultured rat lung fibroblasts isolated from Sprague-Dawley rats, B16BL6 murine melanoma cells, P815 murine mastocytoma cells and MT1A2 murine mammary adenocarcinoma cells.

In a particular preferred embodiment the mammalian host cell is a Chinese hamster ovary (CHO) cell or cell line (Puck et al., 1958, J. Exp. Med. 108: 945-955). Suitable CHO cell lines include e.g. CHO K1 (ATCC CCL-61), CHO pro3−, CHO DG44, CHO P12 or the dhfr− CHO cell line DUK-BII (Chassin et al., PNAS 77, 1980, 4216-4220) or DUXB11 (Simonsen et al., PNAS 80, 1983, 2495-2499).

For introducing the expression vector into an mammalian host cell according to the present invention any transfection technique such as those well-known in the art, e.g. electoporation, calcium phosphate co-precipitation, DEAE-dextran transfection, lipofection, can be employed if appropriate for a given host cell type. It is to be noted that the mammalian host cell transfected with the vector of the present invention is to be construed as being a transiently or stably transfected cell line. Thus, according to the present invention the present mammalian expression vector can be maintained episomally or can be stably integrated in the genome of the mammalian host cell.

A transient transfection is characterised by non-appliance of any selection pressure for a vector borne selection marker. In transient expression experiments which commonly last 20-50 hours post transfection, the transfected vectors are maintained as episomal elements and are not yet integrated into the genome. That is the transfected DNA, does not usually integrate into the host cell genome. The host cells tend to lose the transfected DNA and overgrow transfected cells in the population upon culture of the transiently transfected cell pool. Therefore expression is strongest in the period immediately following transfection and decreases with time. Preferably, a transient transfectant according to the present invention is understood as a cell that is maintained in cell culture in the absence of selection pressure up to a time of 90 hours post transfection.

In a preferred embodiment of the invention the mammalian host cell e.g. the CHO host cell is stably transfected with the mammalian expression vector of the invention. Stable transfection means that newly introduced foreign DNA such as vector DNA is becoming incorporated into genomic DNA, usually by random, non-homologous recombination events. The copy number of the vector DNA and concomitantly the amount of the gene product can be increased by selecting cell lines in which the vector sequences have been amplified after integration into the DNA of the host cell. Therefore, it is possible that such stable integration gives rise, upon exposure to further increases in selection pressure for gene amplification, to double minute chromosomes in CHO cells. Furthermore, a stable transfection may result in loss of vector sequence parts not directly related to expression of the recombinant gene product, such as e.g. bacterial copy number control regions rendered superfluous upon genomic integration. Therefore, a transfected host cell has integrated at least part or different parts of the expression vector into the genome.

A further aspect of the present invention relates to a process for the production of a recombinant protein, comprising the steps of
a) transfecting a mammalian host cell or host cell line with an expression vector, b) culturing the cell under appropriate conditions to enable propagation of the cell and expression of the recombinant protein and secretion of the recombinant protein from the host cell into the medium and c) harvesting the recombinant protein secreted into the medium.

Thus the present invention also relates to a method for the production of a recombinant protein, comprising a) transfecting a mammalian host cell or host cell line with an expression vector, b) culturing the cell under appropriate conditions to enable propagation of the cell and expression of the recombinant protein and secretion of the recombinant protein from the host cell into the medium and c) harvesting the recombinant protein produced from the medium.

Suitable media and culture methods for mammalian cell lines are well-known in the art, as described in U.S. Pat. No. 5,633,162 for instance. Examples of standard cell culture media for laboratory flask or low density cell culture and being adapted to the needs of particular cell types include, without being restricted to, Roswell Park Memorial Institute (RPMI) 1640 medium (Morre, G., The Journal of the American Medical Association, 199, p. 519 f. 1967), L-15 medium (Leibovitz, A. et al., Amer. J. of Hygiene, 78, 1p. 173 ff, 1963), Dulbecco's modified Eagle's medium (DMEM), Eagle's minimal essential medium (MEM), Ham's F12 medium (Ham, R. et al., Proc. Natl. Acad. Sc. 53, p 288 ff. 1965) or Iscoves' modified DMEM lacking albumin, transferrin and lecithin (Iscoves et al., J. Exp. med. 1, p. 923 ff., 1978). For instance, Ham's F10 or F12 media were specially designed for CHO cell culture. Other media specially adapted to CHO cell culture are described in EP-481 791. It is known that such culture media can be supplemented with fetal bovine serum (FBS, also called fetal calf serum FCS), the latter providing a natural source of a plethora of hormones and growth factors. The cell culture of mammalian cells is nowadays a routine operation well-described in scientific textbooks and manuals, it is covered in detail e.g. in R. Ian Fresney, Culture of Animal cells, a manual, 4$^{th}$ edition, Wiley-Liss/N.Y., 2000.

In a preferred embodiment of the present invention the cell culture medium used is devoid of fetal calf serum (FCS or FBS), which then is being termed 'serum-free'. Cells in serum-free medium generally require insulin and transferrin in a serum-free medium for optimal growth. Transferrin may at least partially be substituted by non-peptide chelating agents or siderophores such as tropolone as described in WO 94/02592 or increased levels of a source of an organic iron favorably in conjunction with antioxidants such as vitamin C. Most cell lines require one or more of synthetic growth factors (comprising recombinant polypeptides), including e.g. epidermal growth factor (EGF), fibroblast growth factor (FGF), insulin like growth factors I and II (IGFI, IGFII), etc. Other classes of factors which may be necessary include: prostaglandins, transport and binding proteins (e.g. ceruloplasmin, high and low density lipoproteins, bovine serum albumin (BSA)), hormones, including steroid-hormones, and fatty acids. Polypeptide factor testing is best done in a stepwise fashion testing new polypeptide factors in the presence of those found to be growth stimulatory. Those growth factors are synthetic or recombinant. There are several methodological approaches well-known in animal cell culture, an exemplary being described in the following. The initial step is to obtain conditions where the cells will survive and/or grow slowly for 3-6 days after transfer from serum-supplemented culture medium. In most cell types, this is at least in part a function of inoculum density. Once the optimal hormone/growth factor/polypeptide supplement is found, the inoculum density required for survival will decrease.

In another preferred embodiment, the cell culture medium is protein-free, that is free both of fetal serum and individual protein growth factor supplements or other protein such as recombinant transferrin.

In another embodiment the process of the present invention directed to expression and harvest of the recombinant product protein includes a high-density growth of the animal host cells e.g. in an industrial fed-batch bioreactor. Conventional downstream processing may then be applied. Consequently, a high-density growth culture medium has to be employed. Such high-density growth media can usually be supplemented with nutrients such as all amino acids, energy sources such as glucose in the range given above, inorganic salts, vitamins, trace elements (defined as inorganic compounds usually present at final concentrations in the micromolar range), buffers, the four nucleosides or their corresponding nucleotides, antioxidants such as glutathione (reduced), vitamin C and other components such as important membrane lipids, e.g. cholesterol or phosphatidylcholine or lipid precursors, e.g. choline or inositol. A high-density medium will be enriched in most or all of these compounds, and will, except for the inorganic salts based on which the osmolarity of the essentially isotonic medium is regulated, comprise them in higher amounts (fortified) than the afore mentioned standard media as can be incurred from GB2251 249 in comparison with RPMI 1640. Preferably, a high-density culture medium according to the present invention is fortified in that all amino acids except for tryptophan are in excess of 75 mg/l culture medium. Preferably, in conjunction with the general amino acid requirement, glutamine and/or asparagine are in excess of 1 g/l, more preferably of 2 g/l of high-density culture medium. In the context of the present invention, high-density cell culture is defined as a population of animal cells having temporarily a density of viable cells of at least or in excess of $10^5$ cells/ml, preferably of at least or in excess of $10^6$ cells/ml, and which population has been continuously grown from a single cell or inoculum of lower viable cell density in a cell culture medium in a constant or increasing culture volume.

In a further preferred embodiment the process of the present invention includes a fed-batch culture. A fed-batch culture is a culture system wherein at least glutamine, optionally with one or several other amino acids, preferably glycine, is fed to the cell culture as described in GB2251249 for maintaining their concentration in the medium, apart from controlling glucose concentration by separate feed. More preferably, the feed of glutamine and optionally one or several other amino acids is combined with feeding one or more energy sources such as glucose to the cell culture as described in EP-229 809-A. Feed is usually initiated at 25-60 hours after start of the culture; for instance, it is useful to start feed when cells have reached a density of about $10^6$ cells/ml. It is well known in the art that in cultured animal cells, 'glutaminolysis' (McKeehan et al., 1984, Glutaminolysis in animal cells, in: Carbohydrate Metabolism in Cultured Cells, ed. M. J. Morgan, Plenum Press, New York, pp. 11-150) may become an important source of energy during growth phase. The total glutamine and/or asparagine feed (for substitution of glutamine by asparagine, see Kurano, N. et al., 1990, J. Biotechnology 15, 113-128) is usually in the range from 0.5 to 10 g per 1, preferably from 1 to 2 g per 1 culture volume; other amino acids that can be present in the feed are from 10 to 300 mg total feed per liter of culture, in particular glycine, lysine, arginine, valine, isoleucine and leucine are usually fed at higher amounts of at least 150 to 200 mg as compared to the other amino acids. The feed can be added as shot-addition or as continuously pumped feed, preferably the feed is almost continuously pumped into the bioreactor. It goes without saying that the pH is carefully controlled during fed-batch cultivation in a bioreactor at an approximately physiological pH optimal for a given cell line by addition of base or buffer. When glucose is used as an energy source the total glucose feed is usually from 1 to 10, preferably from 3 to 6 grams per liter of the culture. Apart from inclusion of amino acids, the feed preferably comprises a low amount of choline in the range of 5 to 20 mg per liter of culture. More preferably, such feed of choline is combined with supplementation of ethanolamine essentially as described in U.S. Pat. No. 6,048,728, in particular in combination with feeding glutamine. It goes without saying that upon use of the GS-marker system, lower amounts of glutamine will be required as compared to a non-GS expression system since accumulation of excessive glutamine in addition to the endogenously produced would give rise to ammonia production and concomitant toxicity. For GS, glutamine in the medium or feed is mostly substituted by its equivalents and/or precursors, that is asparagine and/or glutamate.

Methods for harvesting, i.e. isolating and/or purifying a given protein from the medium in which the cells had been cultured are well known in the art.

Preferred embodiments of the invention are illustrated in the figures. What is shown is:

FIG. 1 shows the influence of different signal sequences on the concentration of secreted antibody when used in transient transfections. of CHOK1SV cells. Antibody concentrations achieved by transient transfection of CHOK1SV cells using vectors employing the variant signal sequences. n=6.

Figure 2:
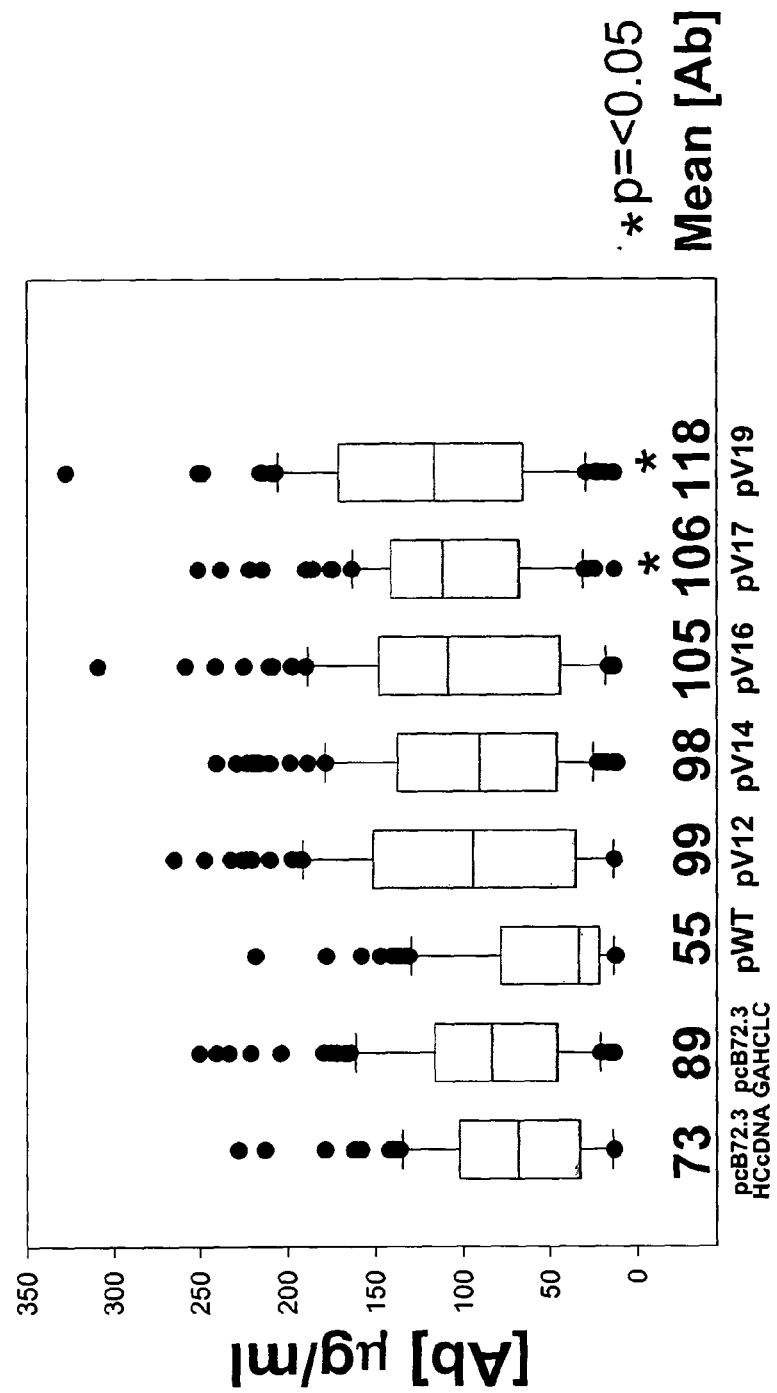

FIG. 2 shows the influence of different signal sequences on the concentration of secreted antibody when used in stable cell lines in static culture. Boxplots show the range of antibody concentrations achieved by stable transfection of CHOK1SV cells using vectors employing the variant signal sequences. Stable GS cell lines were allowed to overgrow for 14 days in 24 well plates at which point antibody concentration was determined by Protein A HPLC. Mean antibody concentrations are shown and those showing a statistically significant increase in mean antibody concentration ($p \leq 0.05$ calculated by ANOVA) are indicated with a *·n=100.

Figure 3:
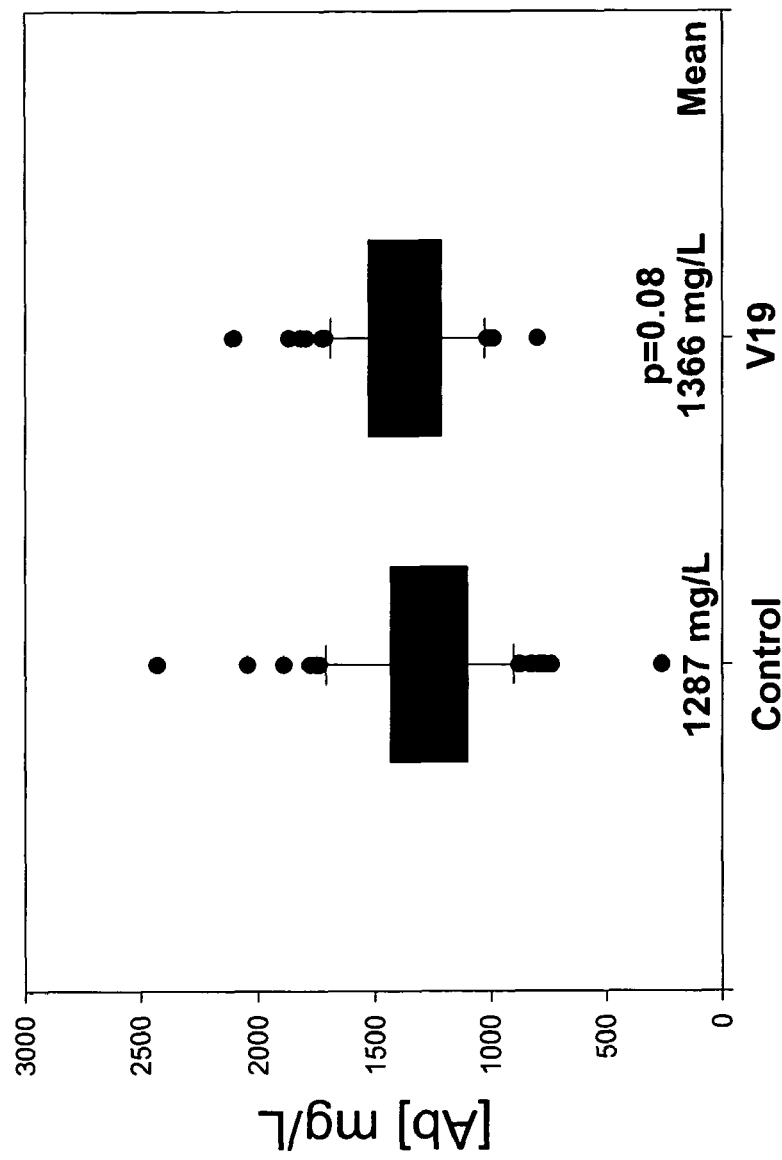

FIG. 3 shows the influence of signal sequence V19 on the concentration of secreted antibody when used in a stable cell line in suspension culture. Boxplots show the range of antibody concentrations achieved by stable transfection of CHOK1SV cells using vectors employing either control or V19 signal sequences. Stable GS cell lines were generated and the top 60 evaluated in a fed-batch process designed to mimic laboratory scale bioreactors. Antibody concentration was determined by Protein A HPLC. Mean antibody concentrations are shown, p value calculated by ANOVA. n=60.

Figure 4:
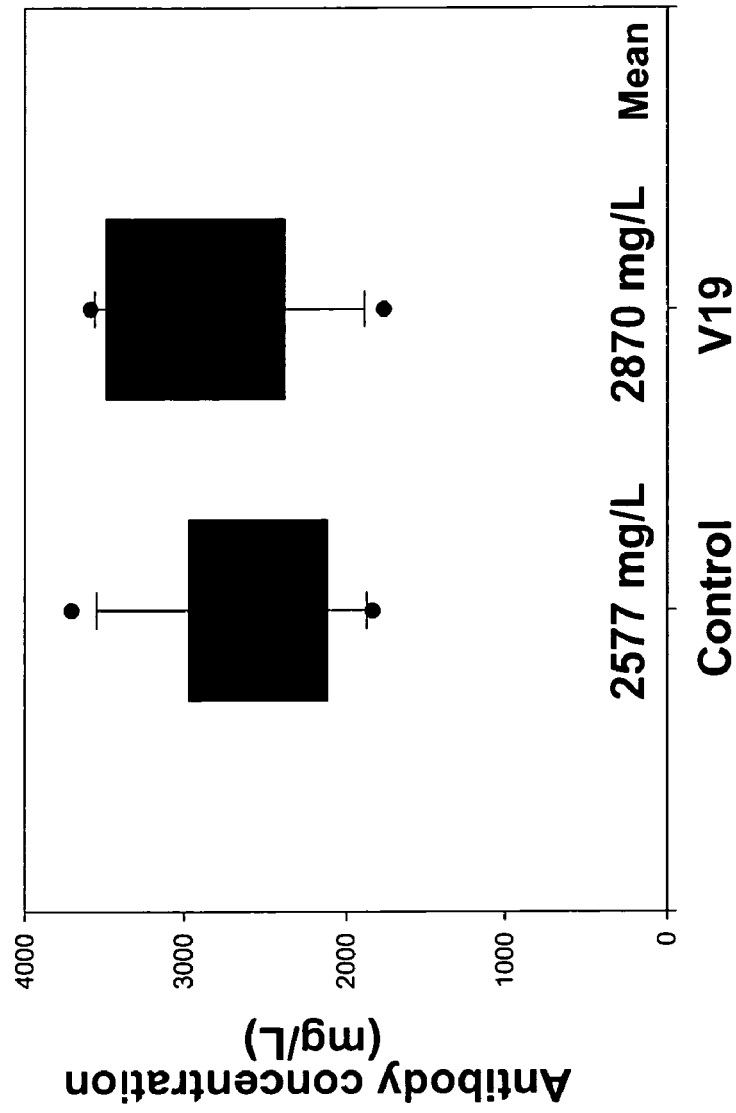

FIG. 4 shows the influence of signal sequence V19 on the concentration of secreted antibody when a stable cell line was cultured in a 10 L Bioreactor. Boxplots show the range of antibody concentrations achieved in 10 L labscale bioreactors using stable cell lines generated using vectors employing either control or V19 signal sequences. Stable GS cell lines were generated and the top 8 evaluated in a fed-batch process. Antibody concentration was determined by Protein A HPLC. Mean antibody concentrations are shown. n=8.

The sequence listing shows:

SEQ ID No.1 shows the amino acid sequence of the signal peptide used in construct pV12. This signal peptide was derived from Sandfly Yellow related protein and is as follows: mrfffvflaivlfqgihg. The signal peptide of SEQ ID No. 1 is also referred to as signal peptide V12.

SEQ ID No.2 shows the nucleic acid sequence encoding the amino acid sequence of signal peptide depicted in SEQ ID No. 2 and is as follows: 5'-atgagattctttttcgtgttcctggccatcgtgctgttccagggcatccacg-3'.

SEQ ID No. 3 shows the amino acid sequence of the signal peptide used in construct pV14. This signal peptide was derived from Silkworm Fibroin LC and is as follows: mkpiflvllvvtsaya. The signal peptide of SEQ ID No. 3 is also referred to as signal peptide V14.

SEQ ID No. 4 shows the nucleic acid sequence encoding the amino acid sequence of the signal peptide depicted in SEQ ID No. 3 and is as follows: 5'-atgaagcccatctttctggtgctgctggtcgtgaccagcgcctacgcc-3'.

SEQ ID No. 5 shows the amino acid sequence of the signal peptide used in construct pV16. This signal peptide was derived from Snake PLA2 and is as follows: mrtlwimavlllgveg. The signal peptide of SEQ ID No. 5 is also referred to as signal peptide V16.

SEQ ID No. 6 shows the nucleic acid sequence encoding the amino acid sequence of the signal peptide depicted in SEQ ID No. 5 and is as follows: 5'-atgaggaccctgtggatcatggccgtgctgctgctgggcgtggagggccaggtg-3'.

SEQ ID No 7 shows the amino acid sequence of the signal peptide used in construct pV17. This signal peptide was derived from Cypridina Noctiluca luciferase and is mktlilavalvycatvhc. The signal peptide of SEQ ID No. 7 is also referred to as signal peptide V17.

SEQ ID No. 8 shows the nucleic acid sequence encoding the amino acid sequence of the signal peptide depicted in SEQ ID No. 7 and is as follows: 5'-atgaaaaccctgatcctggccgtggccctggtgtactgcgccaccgtgcactgc-3'.

SEQ ID No 9 shows the amino acid sequence of the signal peptide used in construct pV19. This signal peptide was derived from Pinemoth Fibroin LC and is mmrpivlvllfatsala. The signal peptide of SEQ ID No. 9 is also referred to as signal peptide V19.

SEQ ID No. 10 shows the corresponding nucleic acid sequence encoding the amino acid sequence of the signal peptide depicted in SEQ ID No. 9 and is as follows: 5'-atgatgaggcccatcgtgctggtgctgctgttcgccacctccgccctggcccaggtg-3'.

The present invention is explained in more detail by the following examples.

Examples

Materials and Methods

Cells Used

CHO cell line CHOK1SV: is a variant of the cell line CHO-K1 and has been adapted to growth in suspension and protein-free medium.

Propagation of CHOK1SV Cells:

CHOK1SV cells were routinely propagated in suspension shaker flasks in CD-CHO medium (Invitrogen) supplemented with 6 mM L-glutamine. Seed concentration was $2 \times 10^5$ cells/ml, and cells are split every 4 days. Flasks were gassed with 5% $CO_2$ and incubated at 36.5° C. (between 35.5° C. and 37.0° C.) with orbital shaking at 140 rpm.

Transient Transfection:

Transient transfections were performed using suspension-growing cells. Cells were counted and distributed onto wells of a 24-well plate at $2.5 \times 10^5$ viable cells per well in a DMEM-based medium supplemented with 10% serum and 6 mM L-glutamine, and incubated overnight at +36.5° C. The following day, the conditioned medium was replaced with 1 mL of fresh medium (as above) and the cells incubated for 3 hours at +37° C.

For each transfection, 5 μg of each of the SGVs (HC and LC-SGVs mixed together) or 5 μg of the DGVs were resuspended in 100 μL transfection medium (OptiMEM, Invitrogen). For positive controls, cells were also transfected with the vector pcB72.3, which encodes heavy chain and light chain genes for an $IgG_4$/kappa antibody which serves as a model antibody. A negative control (water only) was also included.

For each transfection, 5 μL of Lipofectamine-2000 reagent (Invitrogen) was diluted in 100 μL transfection medium, mixed and left to stand for 5 minute at room temperature. The DNA and diluted Lipofectamine reagent were combined, mixed and further left to stand at ambient temperature for 20 minutes. This 200 μL mixture was then added to a well of the 24-well plate containing the cells, and the cells were incubated for 4 or 10 days at +37° C. The culture supernatant was collected and clarified by centrifugation prior to assay for presence of antibody by assembly ELISA.

Stable Transfections for Generation of Static Cultures:

Cells used for transfections were grown in cell suspension culture, as detailed before. Cells from growing cultures were centrifuged and washed once in serum-free medium prior to being re-suspended to a concentration of $1.43 \times 10^7$ cells/mL. A 0.7 mL volume of the cell suspension and 40 μg of plasmid DNA were added to an electroporation cuvette. The cuvette was then placed in the electroporation apparatus and a single pulse of 250 V and 400 μF was delivered. Following transfection, the cells were distributed into 96-well plates at approximately 2,500 host cells/well ($5 \times 10^4$/mL), using the non-selective DMEM-based medium supplemented with 10% dFCS. The plates were incubated at 36.5° C. (between 35.5° C. and 37.0° C.) in an atmosphere of 10% $CO_2$ in air.

The day after the transfection, DMEM-based medium supplemented with 10% dFCS/66 μM L-methionine sulphoximine was added to each well (150 μL/well) to give a final L-methionine sulphoximine concentration of 50 μM. The plates were monitored to determine when the non-transfected cells died and when foci of transfected cells appeared. Foci of transfected cells became apparent approximately three to four weeks after transfection. All the cell lines examined and progressed further came from wells containing only a single colony.

Assessment of Productivity of Cell Lines in Static Culture

The 96-well transfection plates were incubated for approximately three weeks to allow colony formation. The resulting colonies were examined microscopically to verify that the colonies were of a suitable size for assay (covering greater than 60% of the bottom of the well), and that only one colony was present in each well.

Suitable colonies were transferred to wells of 24-well plates containing 1 mL of selective growth medium (DMEM-based medium/10% dFCS/25 μM L-methionine sulphoximine). These cultures were incubated for 14 days at 36.5° C. (between 35.5° C. and 37.0° C.) in an atmosphere of 10% $CO_2$ in air. The supernatant of each well was harvested and analysed for the concentration of antibody present by the protein-A HLPC method.

Assembly ELISA:

The antibody concentration of samples was determined using a sandwich ELISA which measures assembled human IgG. This involved capture of samples and standard onto a 96 well plate coated with an anti-human Fc antibody. Bound antibody is revealed with an anti-human light chain linked to horseradish peroxidase and the chromogenic substrate TMB. Colour development was proportional to the concentration of antibody present in the sample when compared to the standard.

Protein A HPLC:

The Protein A affinity chromatography method for the measurement of IgG was performed on an Agilent 1100 HPLC. IgG product binds selectively to a Poros Protein A immunodetection column. Non-bound material is washed from the column and the remaining bound antibody is released by decreasing the pH of the solvent. The elution was monitored by absorbance at 280 nm and product was quantified (using Chemstation software) against a generic antibody standard and a correction is made for differences in extinction coefficients.

Stable Transfections for Generation of Suspension Cultures:

CHOK1SV host cells were revived from a stock of the CHOK1SV cell line. Cells from subsequent growing cultures were centrifuged and washed once in CD-CHO medium prior to being resuspended at a concentration of $1.43 \times 10^7$ viable cells/mL. For each transfection, approximately 0.7 mL of the cell suspension and 40 μg of plasmid DNA were added to each electroporation cuvette. Four transfections were prepared using the contents of two electroporation cuvettes. Each electroporation cuvette was placed in the electroporation apparatus and a single pulse of 300 V, 900 μF was delivered. Following transfection, the cells from all the required cuvettes were pooled and distributed into 96-well plates at approximately 2,500 host cells/well ($0.50 \times 10^5$/mL) to 10,000 host cells/well ($2.00 \times 10^5$/mL), using the medium CD-CHO/phenol red. Phenol red was added only to indicate cell growth. The plates were incubated at 35.5 to 37.0° C. in an atmosphere of 10% v/v $CO_2$ in air.

The day after transfection, 150 μl of the selective medium (CD-CHO/phenol red/66.6 μM MSX) was added to each well. The final concentration of MSX in each well was 50 μM. The plates were monitored to determine when the non-transfected cells died to leave foci of transfected cells. Foci of transfected cells became apparent three to four weeks after transfection. All the transfectants examined and progressed further came from wells containing only a single colony, as determined by visual assessment.

Selection of Cell Lines for Evaluation in Static Culture:

The 96-well transfection plates were incubated for approximately three to four weeks to allow colony formation. The resulting colonies were examined microscopically to verify that they were of a suitable size for assessment (covering greater than 60% of the bottom of the well), and that only one colony was present in each well. The culture supernatant was removed and assayed for antibody using Lonza's ELISA method. The percentage confluence of the well was assessed at the time of sampling. The value obtained by dividing the assay results by percentage confluence was used to rank the cell lines.

High ranking cell lines were expanded into 24-well plates in the medium CD-CHO/phenol red/25 μM MSX (this medium was used for the entire static culture period). On reaching confluence, this culture was used to inoculate a T25 flask, whilst the remaining culture was re-fed with fresh growth medium and returned to the incubator. When confluence was reached in the T25 flask, this culture was fed with fresh medium to encourage the cells to multilayer and adapt to suspension culture.

For those cell lines progressed from 96-well plates, a second assessment of productivity was undertaken. The 24-well plate cultures that had been progressed and re-fed were incubated for a further fourteen days until confluence or low viability was reached ('overgrown'). At this point, culture supernatant was collected and the antibody concentration measured using a Protein A HPLC method. Cell lines were ranked according to productivity and high ranking cell lines were progressed to be evaluated in suspension culture.

Expansion of Cell Lines to CDACF Suspension Culture:

Suspension cultures were initiated from confluent T25 flask cultures, using the medium CD-CHO/25 µM MSX. The choice of inoculation cell concentration was dependent on the measured viable cell concentration in the T25 flask. If the viable cell concentration was greater than $0.40 \times 10^6$ viable cells/mL, CD-CHO/25 µM MSX medium was added to give a viable cell concentration of $0.20 \times 10^6$ viable cells/mL in a final volume of 5 to 30 mL in a 125 mL shake-flask. If the viable cell concentration was 0.25 to $0.40 \times 10^6$ viable cells/mL, CD-CHO/25 µM MSX medium was added to give a cell concentration of $0.15 \times 10^6$ viable cells/mL in a final volume of 5 to 30 mL in a 125 mL shake-flask. If the viable cell concentration was less than $0.25 \times 10^6$/mL after a maximum of fourteen days in T25 flasks, 10 mL of each culture was automatically progressed into 10 mL of CD-CHO/25 µM MSX medium in 125 mL shake-flasks.

After transfer from static to suspension culture, cell lines were serially subcultured in CD-CHO/25 µM MSX medium on a four day subculture regime, until acceptable and reproducible growth characteristics were attained. Cultures were prepared in 125 mL shake-flasks, containing a 30 mL culture volume, with an initial inoculation cell concentration of 0.05 to $0.20 \times 10^6$ viable cells/mL. Once the viable concentration on day 4 (day of subculture) was consistently above $0.40 \times 10^6$ viable cells/mL, cultures were routinely inoculated at $0.20 \times 10^6$ viable cells/mL.

Fed-Batch Shake-Flask Culture:

Cultures of each selected cell line were prepared in 250 mL shake-flasks with 30 mL of cell suspension using the medium CM42/SPE. The cultures were inoculated at $0.20 \times 10^6$ viable cells/mL and the headspace of each culture was equilibrated with 5% v/v $CO_2$ in air. The cultures were incubated at 35.5 to 37.0° C. on a shaking platform at 140±5 rpm until the viable cell concentration, post peak, was less than or equal to $1.00 \times 10^6$ viable cells/mL or day 15 was reached ('overgrown'). At this point the cultures were harvested.

The cell concentration was determined on days 7 and 14 using a Vi-Cell automated cell counter. On day 3, 2.1 mL of SF40 was added as a bolus to each 30 mL culture. A shot of 360 µL, of the second feed SF41 was applied to the fed-batch cultures on days 8 and 11. Samples of culture supernatant were taken on days 7 and 14 and frozen at −20±5° C. until assayed for assembled antibody by Protein A HPLC.

10 L Bioreactor Culture:

Cell lines were evaluated in 10 L bioreactors. The volume of the sixteen cell line cultures were increased until sufficient volume was obtained to inoculate one 10 liter airlift bioreactor. The volume of inoculum was adjusted to achieve a seed density of approximately $0.2 \times 10^6$ cells/ml. Bioreactors were run for 15 days using a fed-batch strategy. Samples of culture supernatant were taken and assayed for assembled antibody by Protein A HPLC.

Vector Construction

Gene optimised DNA sequences encoding the variable region the cB72.3 antibody were synthesised. As part of the synthesis, a nucleic acid sequence encoding a signal sequence chain was added. In total 19 different signal sequences (sequences V1-V19) were used. Light chain sequences were cloned into the pEE12.4 derived expression vector pConPlusKappa which includes Kappa constant region DNA sequence. Heavy chain were cloned into the pEE6.4 derived vector pConPlusIgG4 which includes IgG4 constant region DNA sequence. Double-gene expression vectors were then generated by cloning Not I/Pvu I fragments of the relevant vector together. The sequence of all constructs was confirmed by DNA sequencing.

As an initial screen, nineteen constructs along with an appropriate control employing the signal sequences routinely used were transiently transfected into the CHOK1SV host cell line using Lipofectamine-2000 (Invitrogen). The constructs were transfected six times and the antibody concentration in the media determined by ELISA. The assay identified that five of the nineteen constructs resulted in dramatically increased mean antibody concentrations over the control with the remaining constructs resulting in either equivalent or reduced antibody concentrations. These constructs were pV12 containing the signal sequence of SEQ ID No. 1 (signal sequence V12), pV14 containing the signal sequence of SEQ ID No. 3 (signal sequence V14), pV16 containing the signal sequence of SEQ ID No. 5 (signal sequence V16), pV17 containing the signal sequence of SEQ ID No. 7 (signal sequence V17), and pV19 containing the signal sequence of SEQ ID No. 9 (signal sequence V19).

The constructs employing the five signal sequences that demonstrated improved expression in the transient transfection system were then used to create stable cell lines in CHOK1SV cells. The antibody concentration in the media from 100 cell lines per construct was determined by Protein A HPLC. The mean antibody concentration from the control cell lines was 89 mg/L. Two of the five signal sequences resulted in cell lines with a statistically significant increase in mean antibody concentration over control cell lines with sequence V17 (SEQ ID No. 7) resulting in a mean antibody concentration of 106 mg/L (19% increase, p=<0.05) and sequence V19 (SEQ ID No. 9) resulting in a mean antibody concentration of 118 mg/L (32% increase, p=<0.05). The data from stable cell lines are depicted in FIG. 1.

When product quality was evaluated by SDS-electrophoresis no gross structural differences were observed between antibodies generated using the control or alternative signal sequences. Assessment of product quality by mass spectroscopy demonstrated that the antibodies generated using the alternative signal sequences were of the expected mass compared to the control suggesting that they were likely to be processed appropriately. This work demonstrates that different signal sequences function with varying efficiency which indicates that the choice of signal sequence is likely to be a key contributor towards optimal antibody expression.

In order to determine if this sequence would lead to an increase in antibody concentration throughout the cell line construction process, constructs were generated encoding the IgG1/kappa antibody version of cB72.3. The constructs used either the gene-optimised genes fused to DNA sequence encoding the signal sequence of SEQ ID No. 9 (V 19) (pcB72.3IgG1V19) or antibody derived signal sequences routinely used (pcB72.3IgG1).

These constructs were stably transfected into CHOK1SV cells. Transfectants were screened in 96-well plates and the high ranking cell lines expanded into 24-well plates. On reaching confluence, the top-60 producers were progressed into T25 flasks and then adapted to suspension in shake-flasks. Productivity was assessed in both batch and fed-batch shake-flask cultures and product quality analysed using culture supernatant from 14-day fed-batch overgrow cultures.

In fed-batch cultures, the construct employing the signal sequence of SEQ ID No. 9 demonstrated a 6% increase in mean antibody concentration compared to controls (p=0.08). Product quality assessment revealed no notable differences between cultures transfected with the control or constructs with the signal sequence of SEQ ID No. 9 (V 19) when analysed by SDS-electrophoresis, IEF, oligosaccharide analysis. Electrospray mass spectroscopy was used to show that the mass of the antibody generated using the V19 sequence was the same as that when generated using the control construct suggesting that the V19 sequence was correct processed during antibody secretion.

In fed-batch bioreactor cultures employing 10 L labscale bioreactors, Sixteen 10 liter laboratory-scale bioreactor cultures were performed. The cell lines reached a wide range of maximum viable cell concentrations. The cell lines containing the signal sequence of SEQ ID No. 9 (V 19) reached between 9.6 and $17.9 \times 10^6$ cells/mL and the control signal sequence cell lines reached between 8.5 and $19.1 \times 10^6$ cells/mL. The average time integral of viable cell concentration (IVC) for the 'new signal sequence' cultures was $2395 \times 10^6$ cells·h/mL whereas the IVC was $2511 \times 10^6$ cells·h/mL for the control cell lines. The average product concentration at harvest was 2870.3 mg/L for the cell lines with signal sequence V19 (SEQ ID NO. 9) and 2577.1 mg/L for the control cell lines. The bioreactor cultures were harvested on day 15.

Based on the laboratory-scale bioreactor cultures it was concluded that the V19 containing cell lines resulted in an increase in mean antibody concentration of 11%, however the difference was not statistically significant due to the wide range of productivities observed.

The invention claimed is:

1. Expression cassette for the secretion of a heterologous protein from a mammalian host cell comprising a promoter, functionally linked to a DNA sequence encoding a signal peptide which is linked in flame to a DNA sequence encoding a heterologous protein, wherein the DNA sequence encoding the signal peptide is selected from SEQ ID NO: 10 or a DNA sequence encoding an amino acid sequence depicted in SEQ ID NO: 9.

2. Mammalian expression vector comprising a promoter, functionally linked to a DNA sequence encoding a signal peptide which is linked in frame to a DNA sequence encoding a heterologous protein, wherein the DNA sequence encoding the signal peptide is selected from SEQ ID NO: 10 or a DNA sequence encoding an amino acid sequence depicted in SEQ ID NO: 9.

3. Mammalian host cell containing a mammalian expression vector according to claim 2.

4. Mammalian host cell according to claim 3 wherein the cell is a Chinese Hamster Ovary (CHO) cell.

5. Process for the production of a recombinant protein, comprising the steps of a) transfecting a mammalian host cell with an expression vector according to claim 2;
b) culturing the host cell under appropriate conditions in a medium to enable propagation of the cell and expression of the recombinant protein and secretion of the recombinant protein from the host cell into the medium; and
c) harvesting the secreted recombinant protein from the medium.

6. Process according to claim 5 wherein the mammalian host cell is a CHO cell.

* * * * *

SEQUENCE LISTING

```
<160> NUMBER OF SEQ ID NOS: 10

<210> SEQ ID NO 1
<211> LENGTH: 18
<212> TYPE: PRT
<213> ORGANISM: Artificial
<220> FEATURE:
<223> OTHER INFORMATION: signal sequence

<400> SEQUENCE: 1

Met Arg Phe Phe Phe Val Phe Leu Ala Ile Val Leu Phe Gln Gly Ile
1               5                   10                  15

His Gly

<210> SEQ ID NO 2
<211> LENGTH: 52
<212> TYPE: DNA
<213> ORGANISM: Artificial
<220> FEATURE:
<223> OTHER INFORMATION: signal sequence

<400> SEQUENCE: 2
atgagattct ttttcgtgtt cctggccatc gtgctgttcc agggcatcca cg          52

<210> SEQ ID NO 3
<211> LENGTH: 16
<212> TYPE: PRT
<213> ORGANISM: Artificial
<220> FEATURE:
<223> OTHER INFORMATION: signal sequence

<400> SEQUENCE: 3

Met Lys Pro Ile Phe Leu Val Leu Leu Val Val Thr Ser Ala Tyr Ala
1               5                   10                  15

<210> SEQ ID NO 4
<211> LENGTH: 48
<212> TYPE: DNA
<213> ORGANISM: Artificial
<220> FEATURE:
<223> OTHER INFORMATION: signal sequence

<400> SEQUENCE: 4
atgaagccca tctttctggt gctgctggtc gtgaccagcg cctacgcc                48

<210> SEQ ID NO 5
<211> LENGTH: 16
<212> TYPE: PRT
<213> ORGANISM: Artificial
<220> FEATURE:
<223> OTHER INFORMATION: signal sequence
```

```
<400> SEQUENCE: 5

Met Arg Thr Leu Trp Ile Met Ala Val Leu Leu Leu Gly Val Glu Gly
1               5                   10                  15

<210> SEQ ID NO 6
<211> LENGTH: 54
<212> TYPE: DNA
<213> ORGANISM: Artificial
<220> FEATURE:
<223> OTHER INFORMATION: signal sequence

<400> SEQUENCE: 6
atgaggaccc tgtggatcat ggccgtgctg ctgctgggcg tggagggcca ggtg          54

<210> SEQ ID NO 7
<211> LENGTH: 18
<212> TYPE: PRT
<213> ORGANISM: Artificial
<220> FEATURE:
<223> OTHER INFORMATION: signal sequence

<400> SEQUENCE: 7

Met Lys Thr Leu Ile Leu Ala Val Ala Leu Val Tyr Cys Ala Thr Val
1               5                   10                  15
His Cys

<210> SEQ ID NO 8
<211> LENGTH: 54
<212> TYPE: DNA
<213> ORGANISM: Artificial
<220> FEATURE:
<223> OTHER INFORMATION: signal sequence

<400> SEQUENCE: 8
atgaaaaccc tgatcctggc cgtggccctg gtgtactgcg ccaccgtgca ctgc          54

<210> SEQ ID NO 9
<211> LENGTH: 17
<212> TYPE: PRT
<213> ORGANISM: Artificial
<220> FEATURE:
<223> OTHER INFORMATION: signal sequence

<400> SEQUENCE: 9

Met Met Arg Pro Ile Val Leu Val Leu Leu Phe Ala Thr Ser Ala Leu
1               5                   10                  15
Ala

<210> SEQ ID NO 10
<211> LENGTH: 57
<212> TYPE: DNA
<213> ORGANISM: Artificial
<220> FEATURE:
<223> OTHER INFORMATION: signal sequence

<400> SEQUENCE: 10
atgatgaggc ccatcgtgct ggtgctgctg ttcgccacct ccgccctggc ccaggtg       57
```